(12) United States Patent
Shaw et al.

(10) Patent No.: US 11,141,570 B2
(45) Date of Patent: Oct. 12, 2021

(54) IV CATHETER WITH RETRACTABLE NEEDLE AND LATERALLY OFFSET BIASING ELEMENT AND NEEDLE RETRACTION CAVITY

(71) Applicants: Retractable Technologies, Inc., Little Elm, TX (US); Thomas J. Shaw, Frisco, TX (US)

(72) Inventors: Thomas J. Shaw, Frisco, TX (US); Mark Small, Heavener, OK (US); Ni Zhu, Plano, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 0 days.

(21) Appl. No.: 15/940,279

(22) Filed: Mar. 29, 2018

(65) Prior Publication Data

US 2019/0298973 A1 Oct. 3, 2019

(51) Int. Cl.
*A61M 25/06* (2006.01)
*A61B 5/15* (2006.01)
*A61M 5/32* (2006.01)

(52) U.S. Cl.
CPC ..... *A61M 25/0631* (2013.01); *A61B 5/15003* (2013.01); *A61B 5/150992* (2013.01); *A61M 25/065* (2013.01); *A61M 25/0618* (2013.01); *A61M 25/0606* (2013.01); *A61M 25/0612* (2013.01); *A61M 25/0625* (2013.01); *A61M 25/0637* (2013.01); *A61M 25/0643* (2013.01); *A61M 25/0693* (2013.01); *A61M 2005/3227* (2013.01); *A61M 2005/3241* (2013.01); *A61M 2025/0656* (2013.01); *A61M 2205/75* (2013.01); *A61M 2205/7536* (2013.01)

(58) Field of Classification Search
CPC ........... A61M 25/0631; A61M 25/065; A61M 25/0606; A61M 25/0693; A61M 2205/75; A61M 25/0612; A61M 25/0637; A61M 25/0643; A61M 25/01612; A61M 25/0618; A61M 25/0625; A61M 2205/7536; A61M 2025/0656; A61B 5/150992; A61B 5/15003
See application file for complete search history.

(56) References Cited

U.S. PATENT DOCUMENTS 5,779,679 A 7/1998 Shaw
5,871,058 A 2/1999 Naccarato et al.
(Continued)

FOREIGN PATENT DOCUMENTS

WO WO2018049413 3/2018

*Primary Examiner* — Nathan R Price
*Assistant Examiner* — Tania Ismail
(74) *Attorney, Agent, or Firm* — Monty L Ross PLLC; Monty L. Ross (57) ABSTRACT

An intravenous catheter introducer for medical use having a body, a frontal attachment that is disposed in transverse sliding engagement with a front part of the body, a hub tube assembly that is releasably supported by the frontal attachment, and a retractable catheter insertion needle and needle holder that are biased rearwardly by a spring offset laterally from the needle axis, whereby lateral repositioning of the body relative to the frontal attachment following vascular insertion moves a needle retraction cavity disposed inside the body into substantial coaxial alignment and causes the needle holder to be retracted into the needle retraction cavity.

10 Claims, 10 Drawing Sheets

(56) References Cited

U.S. PATENT DOCUMENTS

| | | | |
|---|---|---|---|
| 5,989,220 A * | 11/1999 | Shaw | ............... A61M 25/0631 |
| | | | 604/110 |
| 6,210,371 B1 | 4/2001 | Shaw | |
| 6,872,193 B2 | 3/2005 | Shaw et al. | |
| 7,740,615 B2 | 6/2010 | Shaw et al. | |
| 8,048,031 B2 | 11/2011 | Shaw et al. | |
| 9,308,353 B2 * | 4/2016 | Shaw | ............... A61M 25/0693 |
| 9,550,030 B2 | 1/2017 | Zivkovic et al. | |
| 9,694,139 B2 | 7/2017 | Shaw et al. | |
| 9,808,602 B2 | 11/2017 | Shaw et al. | |
| 9,814,841 B2 | 11/2017 | Shaw et al. | |
| 2016/0310057 A1 * | 10/2016 | Shaw | ............... A61B 5/150656 |
| 2018/0008181 A1 | 1/2018 | Shaw et al. | |

* cited by examiner

IV CATHETER WITH RETRACTABLE NEEDLE AND LATERALLY OFFSET BIASING ELEMENT AND NEEDLE RETRACTION CAVITY

BACKGROUND OF THE INVENTION

1. Field of the Invention

This invention relates to medical devices, and more particularly to an intravenous ("IV") catheter introducer having a body, a selectively retractable, forwardly projecting catheter insertion needle and a detachable hub.

2. Description of Related Art

Intravenous catheter introducers with retractable needles have previously been disclosed, for example, in U.S. Pat. Nos. 5,817,058; 5,779,679; 5,989,220; 6,210,371; 6,872,193; 7,740,615; and 8,048,031. Such devices typically comprise a hub with a forwardly extending flexible catheter through which a needle tip projects slightly during insertion of the needle tip and catheter into a vein. Following insertion, the needle is withdrawn or retracted into the body of the device, which is then separated from the hub, allowing the flexible catheter to remain in place inside the vein. While manual pressure is applied to the vein just forwardly of the catheter tip to restrict blood flow, another infusion line is attached to the hub for use in delivering fluid through the catheter and into the vascular system of a patient.

During retraction of the catheter insertion needle, a basing force is typically applied to the needle holder to drive or draw the needle rearwardly into a needle retraction cavity where it no longer poses a risk of accidental needle stick injuries to healthcare workers. The needle retraction cavity is often coaxially aligned with the longitudinal axis through the insertion needle and the needle holder. The biasing force can be applied, for example, by a biasing element operating in tension or compression, or can be applied manually through a lever, guide or mechanical linkage that causes the needle holder and insertion needle to move rearwardly from a position where the needle tip projects forwardly through a flexible catheter connected to a catheter hub to a retracted and more protected position in which the catheter introducer can be separated from the catheter hub without risk of injury.

In many such devices, a coil spring is coaxially aligned with and disposed around a tubular shaft portion of the needle holder. Prior to introducing a forwardly projecting needle into a patient's vein, the coil spring is held in compression and biases the needle rearwardly relative to a flexible catheter tube that is carried by the needle into the patient's vein. Following vascular insertion and prior to use of the catheter tube for infusing fluid, the compressed spring is released to drive the needle holder and needle rearwardly into a needle retraction cavity disposed in the body of the device.

Other medical devices comprising retractable needles with coaxially aligned biasing elements and laterally slidable components are disclosed, for example, in U.S. Pat. Nos. 9,138,545; 9,302,055; 9,308,353; 9,320,469; 9,381,309; and 9,808,602, and in United States Patent Publication Nos. 2014/0171876; 2016/0310057; 2016/0317756. In such devices, the elements biasing the needles are believed to be coaxially aligned with the needle and needle holder prior to and during needle retraction.

SUMMARY OF THE INVENTION

An IV catheter introducer is disclosed that comprises a body and a catheter insertion needle biased rearwardly by a spring that is offset laterally from the catheter insertion needle. Needle retraction is initiated by lateral movement of the body relative to the catheter insertion needle following vascular insertion.

One embodiment of the invention is an IV catheter introducer comprising a body and a frontal attachment that is disposed forwardly of and slidably engages the body along an axis that is transverse to a longitudinal axis through the body.

One embodiment of the invention is an IV catheter introducer comprising a body, a frontal attachment mounted in transverse sliding relation to a front part of the body, and a needle hub releasably supported by the frontal attachment.

One embodiment of the invention is an IV catheter introducer comprising a body, a frontal attachment that engages and is laterally moveable relative to the body, and a needle holder assembly disposed in longitudinal sliding engagement with and seated inside the frontal attachment.

One embodiment of the invention is an IV catheter introducer comprising an insertion needle that is biased rearwardly by a compressed spring having a longitudinal axis that is offset laterally from the longitudinal axis through the insertion needle.

One embodiment of the invention is an IV catheter introducer comprising a forwardly projecting needle that is rearwardly biased by a spring offset laterally from a longitudinal axis through the needle to facilitate withdrawal of the needle from a patient following vascular insertion.

One embodiment of the invention is an IV catheter introducer comprising a needle holder assembly that further comprises a base, a tubular needle holder projecting forwardly from the base, an insertion needle disposed in substantially fixed relation to and projecting forwardly from the tubular needle holder, a substantially cylindrical spring post projecting forwardly from the base in parallel and spaced-apart relation to the tubular needle holder, and a coiled spring disposed around the spring post that is compressible during assembly to bias the base of the needle holder rearwardly during retraction of the insertion needle.

One embodiment of the invention is an IV catheter introducer comprising a selectively removable fluid sampling tool disposed inside a longitudinally extending fluid chamber disposed in the body of the device.

One embodiment of the invention is an IV catheter introducer comprising a body with oppositely facing, substantially flat, pad-printable surfaces.

One embodiment of the invention comprises an IV catheter introducer having a body, a frontal attachment slidably engaging the body in a plane transverse to the needle axis, a needle hub, and a selectively removable needle cap with a locking member configured to prevent relative sliding movement between the body and the frontal attachment prior to removal of the needle cap for vascular insertion.

One embodiment of the invention is an IV catheter introducer comprising a retractable catheter insertion needle and a needle retraction spring that are laterally offset from each other during vascular insertion.

One embodiment of the invention is an IV catheter introducer comprising a retractable catheter insertion needle and a needle retraction cavity that are laterally offset from each other during vascular insertion.

One embodiment of the invention is an IV catheter introducer comprising a fluid sampling tool further comprising a tool body, a sampling tip, a fluid sample reservoir, a filter housing communicating with the fluid sample reservoir, and a filter seated inside a proximal end of the filter housing.

These and other features of the present invention will be better understood from a consideration of the following detailed description of various embodiments and appended claims in conjunction with the accompanying drawings.

As used throughout this document, "distal" refers to the forwardly facing end of a part or element of the device and "proximal" refers to the rearwardly facing end of a part or element of the device. As a general matter in a typical use environment, the distal end is the end nearest the tip of the forwardly facing needle and the proximal end is the end oppositely disposed from the distal end.

BRIEF DESCRIPTION OF THE DRAWINGS

The syringe of the invention is further described and explained in relation to the following drawings wherein.

DESCRIPTION OF PREFERRED EMBODIMENTS

Referring to FIGS. 1-11, a satisfactory embodiment of IV catheter introducer 20 of the invention comprises body 22, frontal attachment 24, selectively removable needle cap 26, fluid sampling tool 28, filter 30, needle holder assembly 32, fluid seal 34, coil spring 36, insertion needle 38 and hub tube assembly 40. Body 22 further comprises front wall 50 with cylindrical opening 52 defining a recess into which annular fluid seal 34 comprising tubular bore 60 is seated (FIGS. 2 and 5) during assembly. Still referring to FIGS. 2 and 5, front wall 50 further comprises elongate opening 54 that is offset laterally from cylindrical opening 52 and provides access to needle retraction chamber 118 (FIG. 5) bounded by walls 48 and closed proximal end wall 120. Front wall 50 of body 22 is bounded on the top and bottom by lower and upper edges 51, 53, respectively that extend transversely to a longitudinal axis through insertion needle 38 and are desirably configured to slidably engage corresponding recesses 82, 80 in slide member 76 of frontal attachment 24. Positioning ramp 55 of body 22 is provided to assist in the lateral positioning of body 22 relative to slide member 76 of frontal attachment 24 when locking member 108 of needle cap 26 (FIG. 2) is not yet installed or is selectively removed prior to vascular insertion of insertion needle 38. Textured touch surfaces 56, 58 of body 22 are desirably provided to facilitate grasping of body 22 during use.

Figure 1:
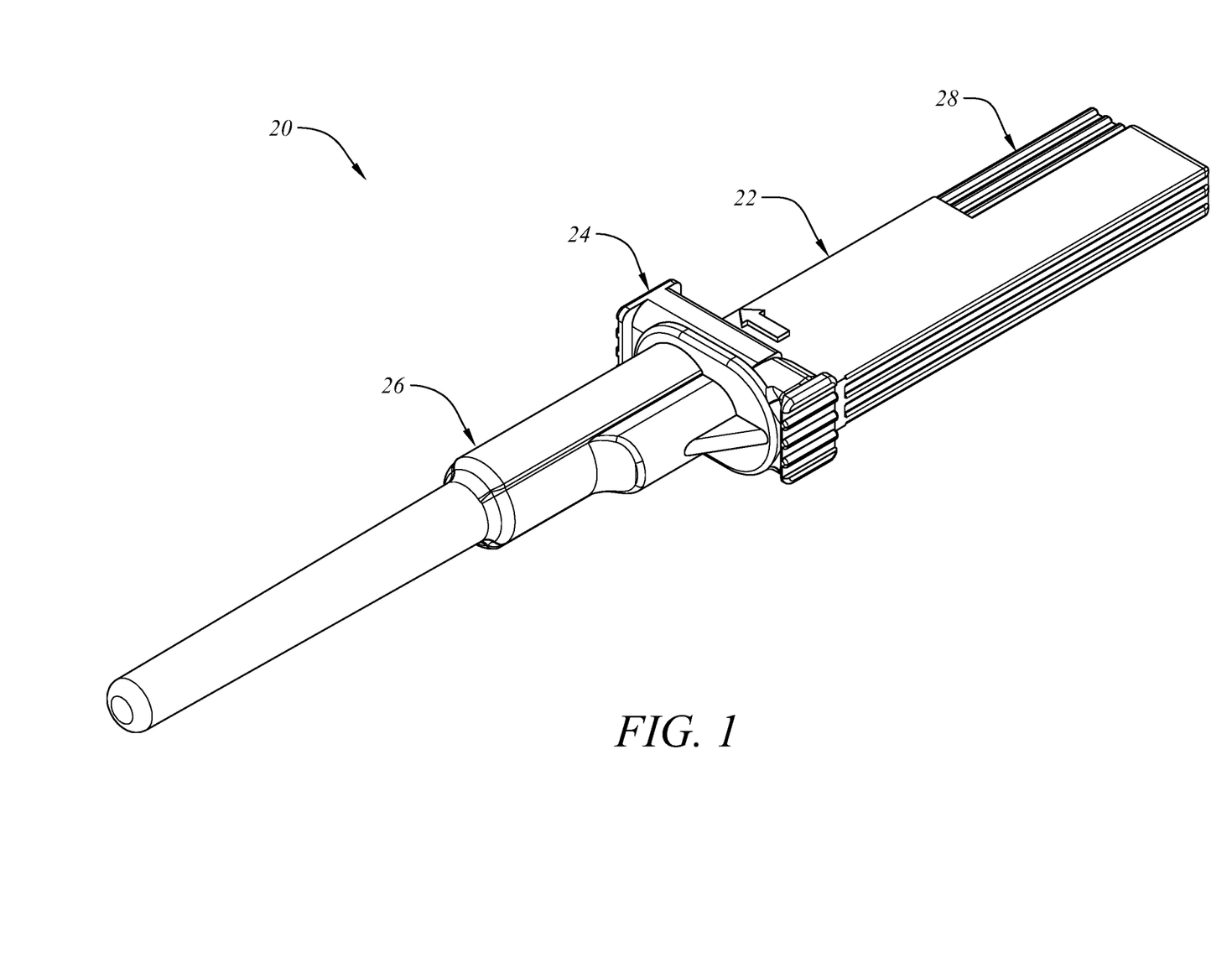
FIG. 1 is a top front perspective view of one embodiment of the IV catheter introducer of the invention in which the needle cap (including the locking member) is installed, with the locking member of the needle cap restricting lateral sliding movement of the body relative to the frontal attachment prior to use.
Figure 2:
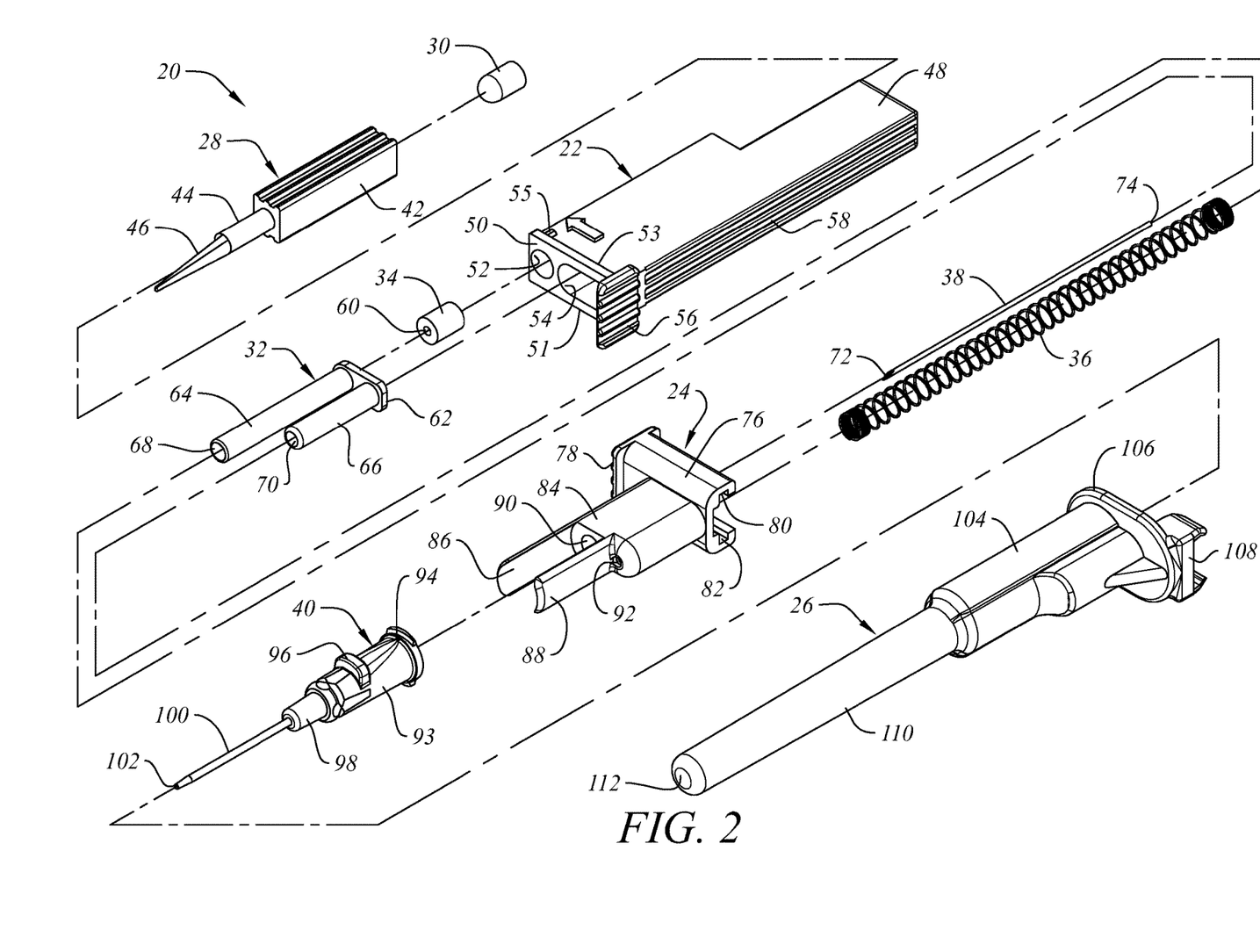
FIG. 2 is an exploded top front perspective view of the embodiment of FIG. 1.
Figures 3, 4:
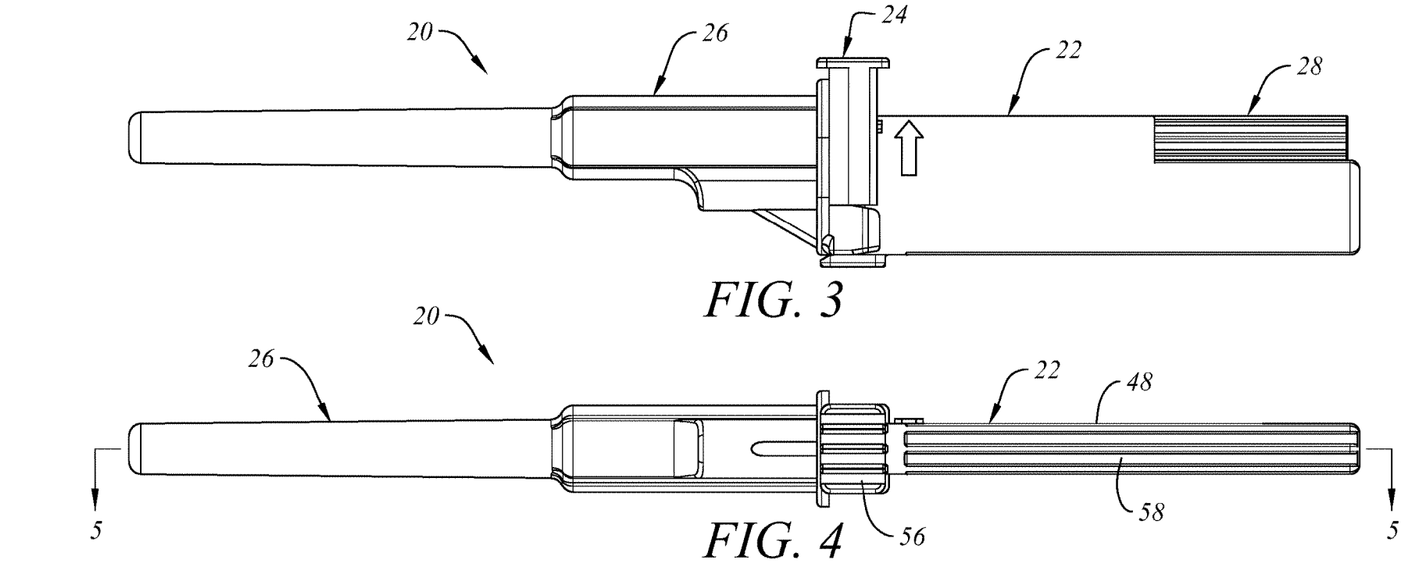
FIG. 3 is a top plan view of the embodiment of FIG. 1.
FIG. 4 is a right side elevation view of the embodiment of FIG. 3.
Figure 5:
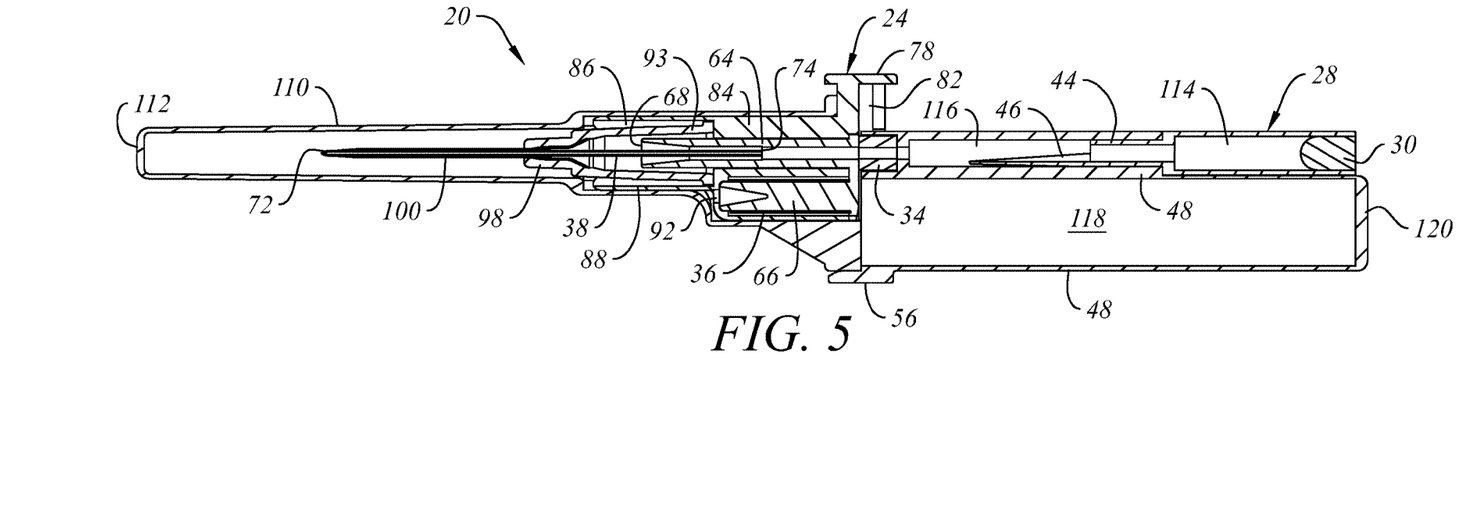
FIG. 5 is a cross-sectional view taken along line 5-5 of FIG. 4.
Figure 6:
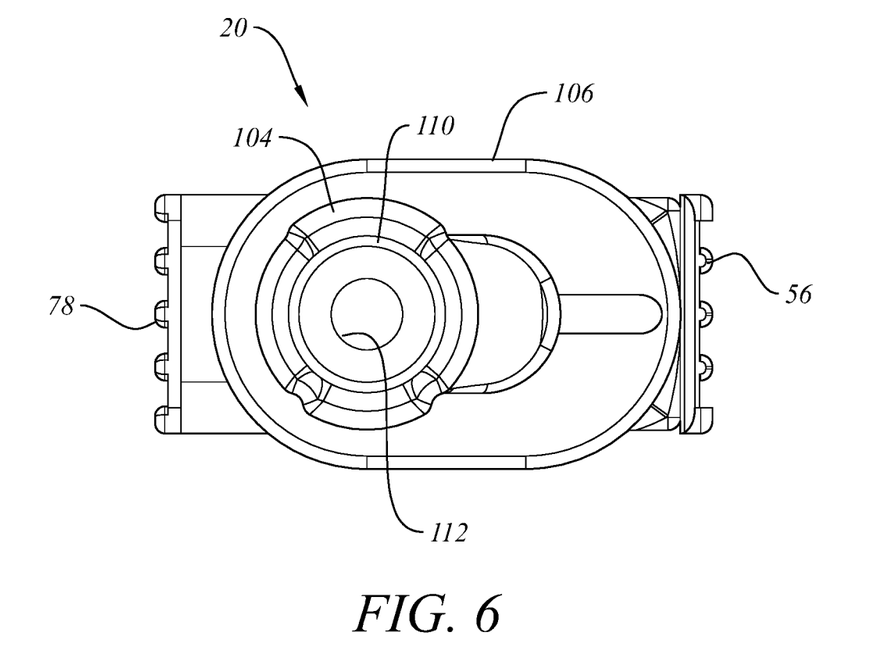
FIG. 6 is a front elevation view of the embodiment of FIG. 1.
Figure 7:
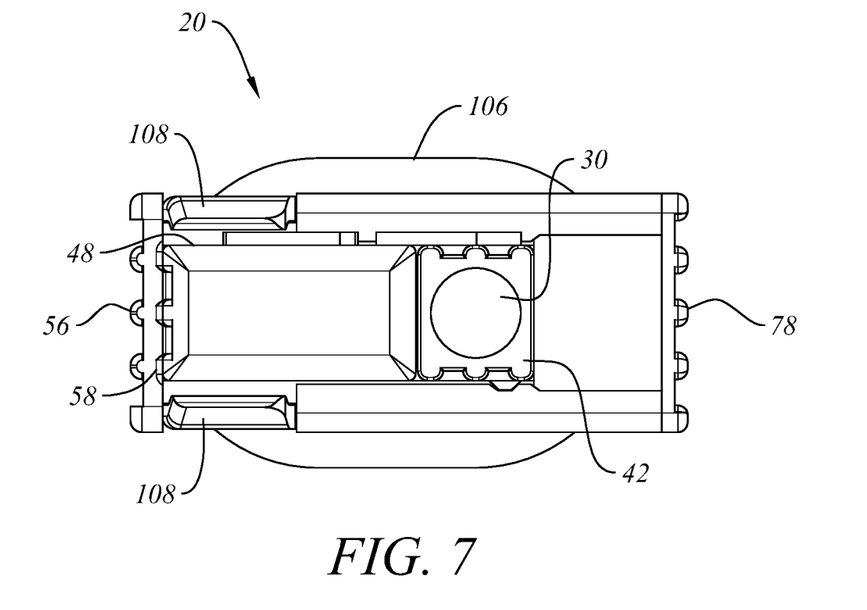
FIG. 7 is a rear elevation view of the embodiment of FIG. 6.
Figure 8:
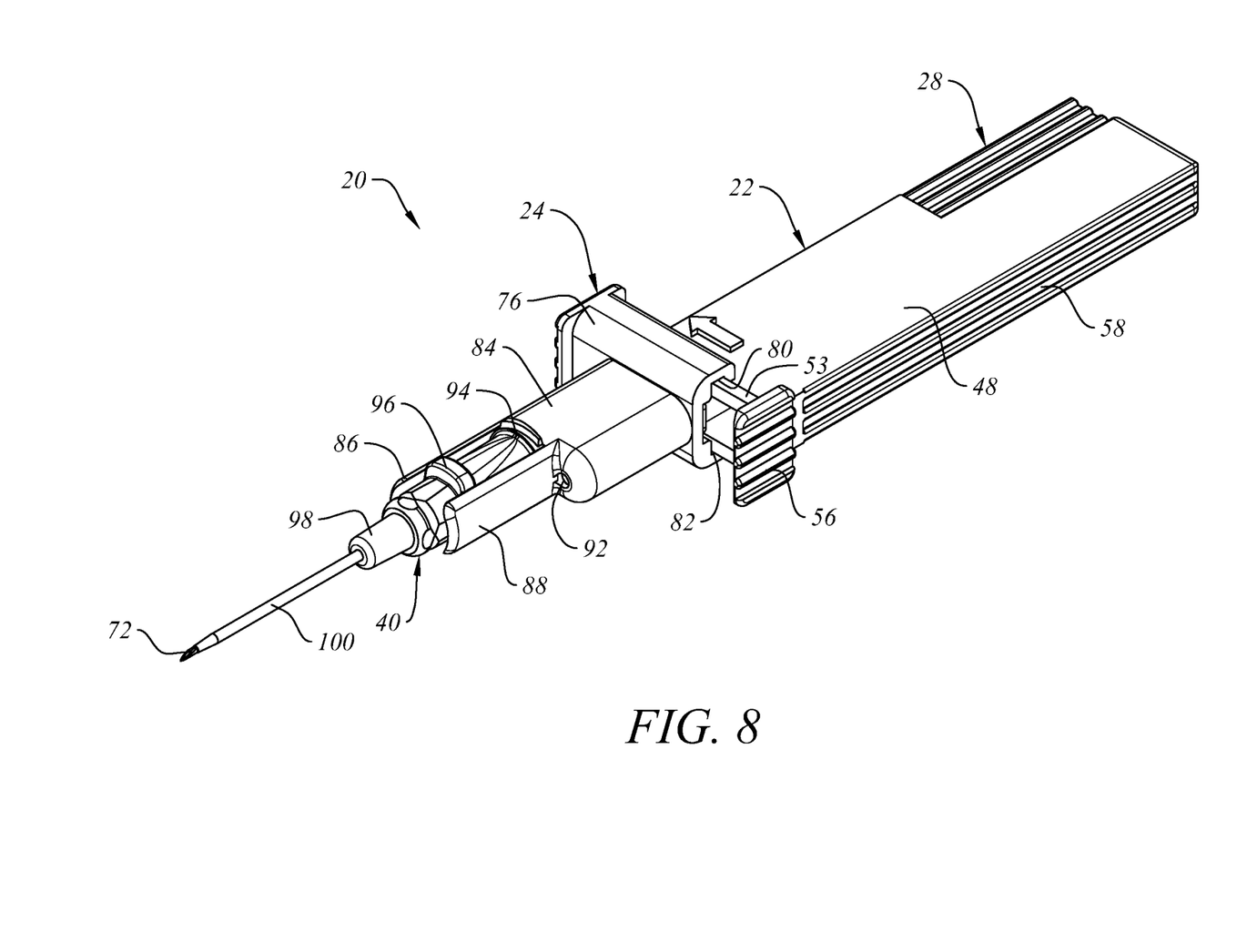
FIG. 8 is a top front perspective view of the embodiment of FIG. 1 with the needle cap removed.
Figure 9:
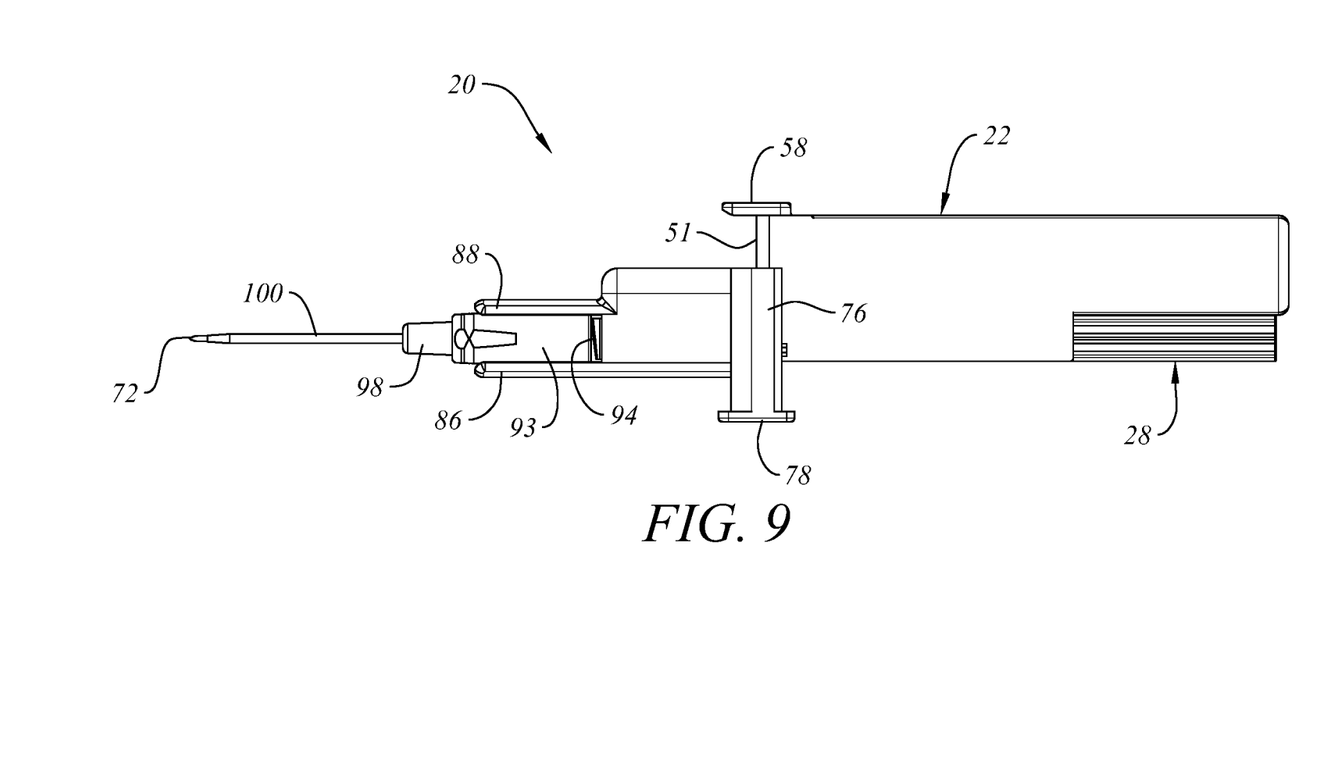
FIG. 9 is a bottom plan view of the embodiment of FIG. 8.
Figure 10:
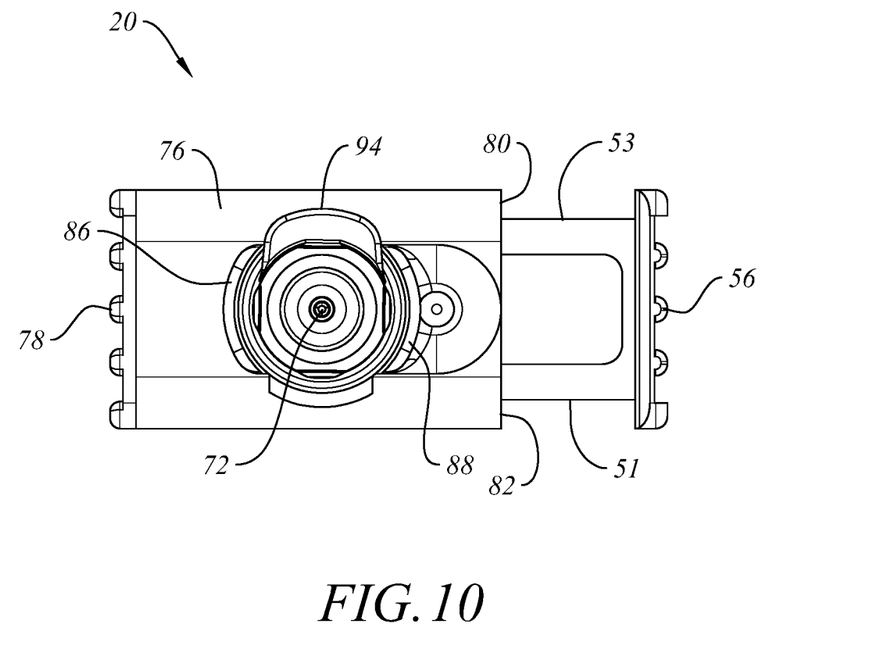
FIG. 10 is a front elevation view of the embodiment of FIG. 8.
Figure 11:
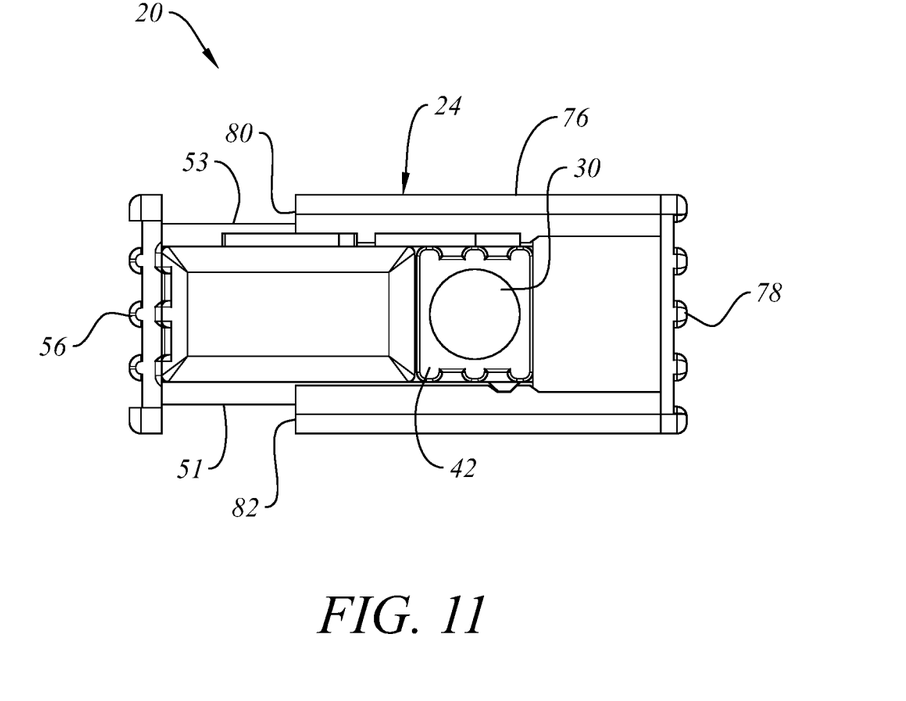
FIG. 11 is a rear elevation view of the embodiment of FIG. 8.
Figure 12:
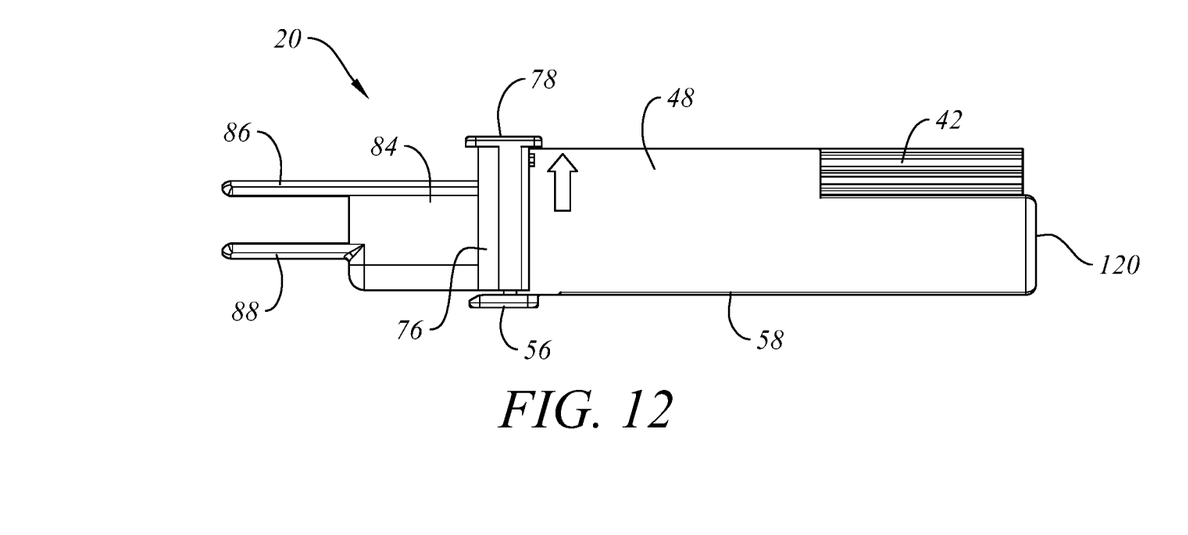
FIG. 12 is a top plan view of the body and frontal attachment portions of the embodiment of FIG. 8 following retraction of the insertion needle and separation of the needle hub from the frontal attachment.
Figure 13:
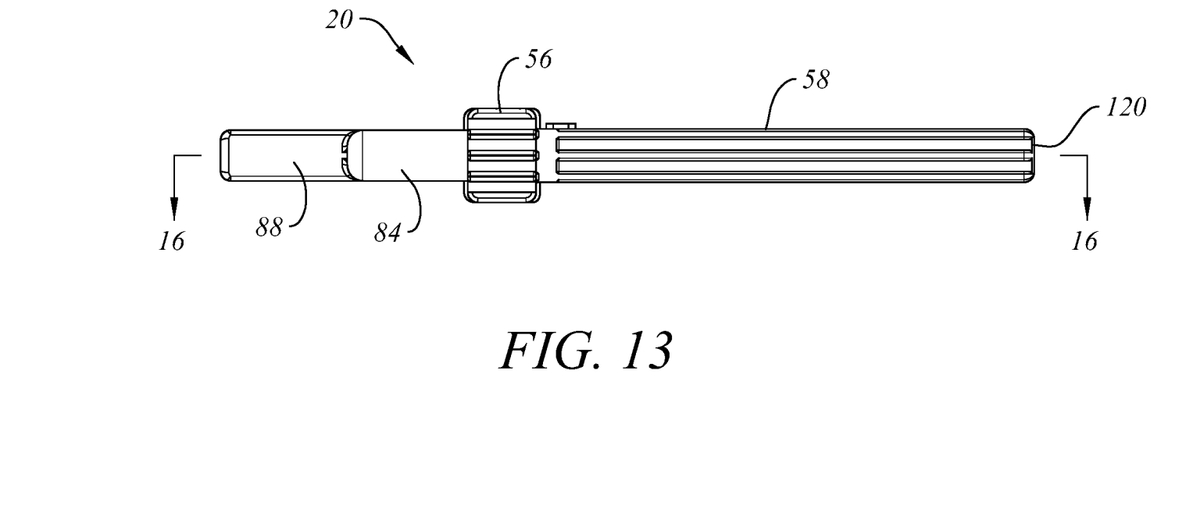
FIG. 13 is a right side elevation view of the embodiment of FIG. 12.
Figure 14:
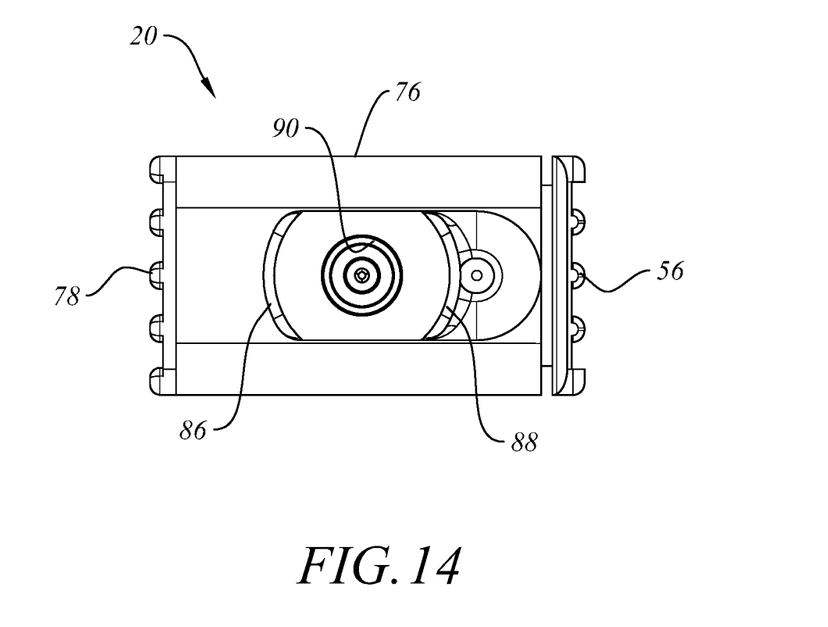
FIG. 14 is a front elevation view of the embodiment of FIG. 12.
Figure 15:
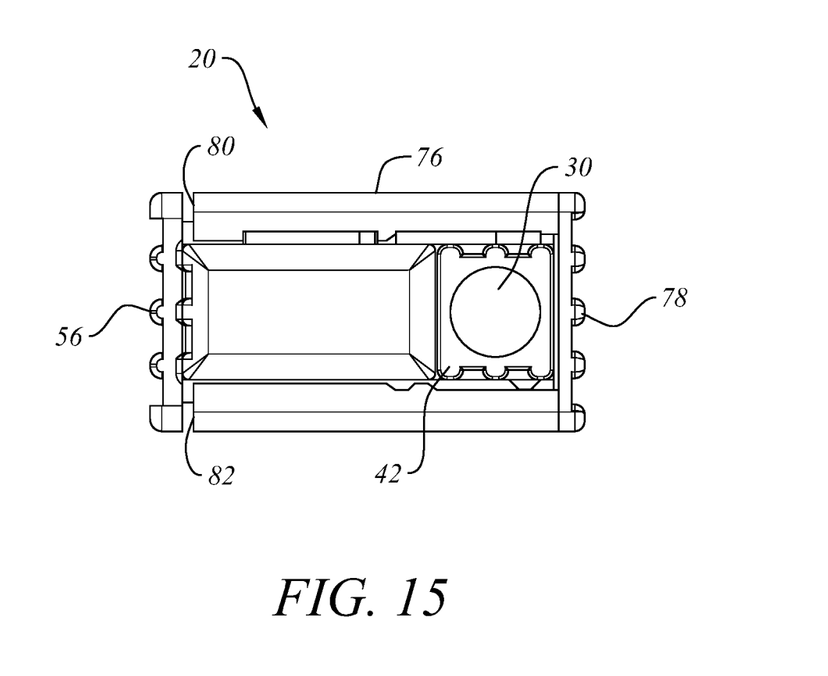
FIG. 15 is a rear elevation view of the embodiment of FIG. 12.
Figure 16:
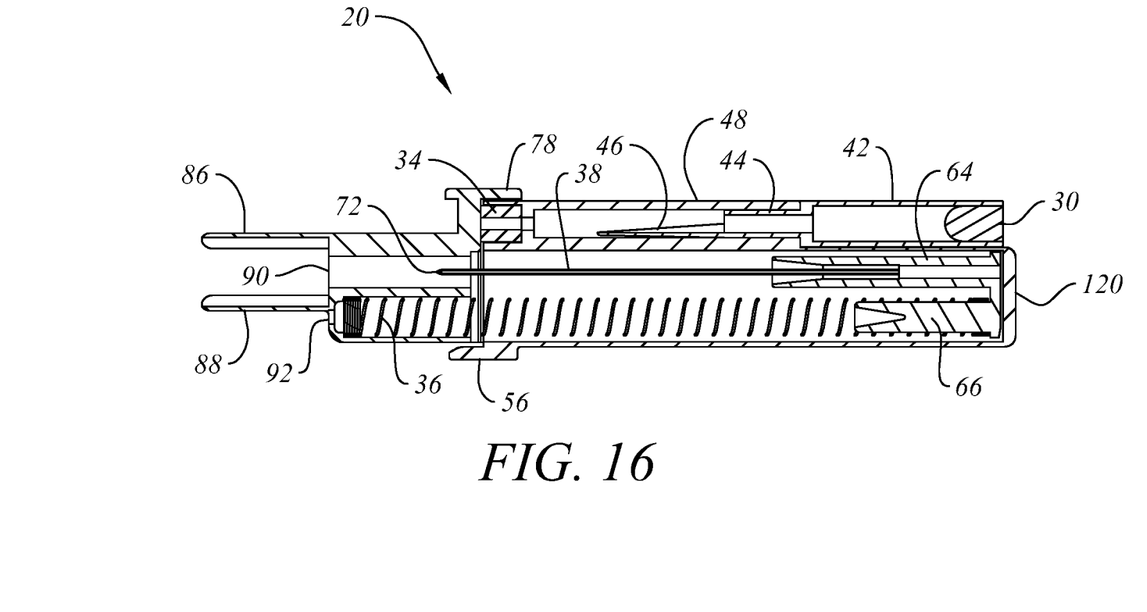
FIG. 16 is a cross-sectional view taken along line 16-16 of FIG. 15.

Still referring to FIGS. 1-11, frontal attachment 24 further comprises slide member 76 with laterally extending recesses 80, 82 as referred to above and textured touch surface 78 disposed at the side opposite touch surface 56 of body 22 (FIG. 2) when frontal attachment 24 is slidably engaged with front wall 50 (as shown with and without needle cap 26 in FIGS. 1 and 8). Frontal attachment 24 further comprises needle holder support housing 84 projecting forwardly from slide member 76. In the embodiment shown, needle support housing 84 is configured to receive and support needle holder assembly 32 (FIG. 2), which desirably further comprises base 62 having substantially tubular needle holder 64 and spring support post 66 projecting forwardly from base 62 in substantially parallel and laterally spaced-apart relation. Open distal end 90 of needle support housing 84 is cooperatively aligned with open distal end 68 of needle holder 64 to facilitate insertion of insertion needle 38, which then projects forwardly through hub tube assembly 40 during assembly of IV catheter introducer 20 (FIGS. 5 and 8). Vent opening 92 in needle support housing 84 is desirably cooperatively aligned with tapered recess 70 disposed in the distal end of spring support post 66 of needle support housing 84. During assembly of IV catheter introducer 20, spring support post 66 of needle holder assembly 32 is desirably inserted into the proximal end of coil spring 36 and the distal end of coil spring 36 is inserted into needle support housing 84 and then compressed as needle holder assembly 32 is inserted into frontal attachment 24. Proximal end 74 of insertion needle 38 can be inserted into the distal end 68 of needle holder 64 either before or after needle holder assembly 32 is inserted into and seated inside frontal attachment 24.

In the embodiment shown, insertion needle 38 is inserted through hub 93, cannula support 98 and flexible cannula tube 100 of hub tube assembly 40 in such manner that distal needle tip 72 projects slightly through closely spaced distal opening 102 so as to be carried by needle tip 72 into a patient's vein during vascular insertion. Following vascular insertion, needle 38 is withdrawn rearwardly through flexible cannula tube 100, cannula support 98 and hub 93 either prior to or, more preferably, during retraction of needle 38 into frontal attachment 24 and body 22 of IV catheter introducer 20. Hub tube assembly 40 further comprises luer lock 94 or another similarly effective structure for use in attaching hub 93 to a fluid flow line following separation of hub 93 from frontal attachment 24 following vascular insertion and withdrawal or retraction of insertion needle 38 from hub tube assembly 40. In one preferred embodiment of the invention (FIGS. 2 and 8), laterally opposed hub guides 86, 88 are desirably provided to properly position and support hub tube assembly 40 in relation to frontal attachment 24 prior to and during vascular insertion of insertion needle 38.

Laterally projecting boss 96 (FIG. 2) is desirably provided for use in positioning hub 93 relative to hub guides 86, 88 prior to vascular insertion and for use in separating hub tube assembly 40 from frontal attachment 24 following vascular insertion.

Still referring to FIGS. 1-11, fluid sampling tool 28 is optionally provided for use in obtaining small, droplet-sized samples of blood or any other bodily fluid that enters fluid chamber 116 of body 22 (FIG. 5) incidental to vascular insertion or other use of IV catheter introducer 20. As depicted in this embodiment, fluid sampling tool 28 further comprises tool body 42 with fluid sample reservoir 44 disposed in fluid communication with forwardly projecting fluid sampling tip 46, which is disposed in fluid communication with fluid chamber 116 (FIG. 5) behind annular fluid seal 34 in body 22. Filter 30 is desirably insertable into tubular bore 114 from the rear of fluid sampling tool 28. According to one embodiment of the invention, the outer wall of fluid sample reservoir 44 frictionally engages the inside wall of fluid chamber 116 of body 22 to maintain fluid sampling tool 28 in place when not in use.

Referring to FIGS. 1-8, selectively removable needle cap 26 further comprises cap body 104 projecting forwardly from integrally molded base flange 106. Cap body 104 is desirably sized and configured to frictionally engage the outside walls of frontal attachment 32 and hub guides 86, 88. Cap body 104 and forwardly projecting tapered nose 110 with closed end 112 are desirably provided to protect hub tube assembly 40 and insertion needle 38 from contamination or damage prior to use. Locking member 108 is desirably provided rearwardly of base flange 106 to prevent body 22 from moving laterally relative to frontal attachment 24 prior to removal of needle cap 26 prior to use of IV catheter introducer 20.

Referring to FIGS. 2 and 12-16 (in which similarly identified parts bear reference numerals consistent with those previously discussed above), at any time following vascular insertion, insertion needle 38 can be retracted from hub tube assembly 40 and into body 22 and frontal attachment 24 so that needle tip 72 is no longer exposed to a patient, healthcare workers or subsequent handlers of IV catheter introducer 20 during waste disposal. Needle retraction is achieved by applying oppositely directed manual pressure to oppositely facing touch surfaces 56, 78 so that body 22 is moved laterally relative to frontal attachment 24 in a direction that is transverse to the longitudinal axis through insertion needle 38. When this lateral movement occurs, base 62 of needle holder assembly 32 is moved into alignment with needle retraction chamber 118. When so aligned, no further resistance is applied to base 62 by front wall 50 of body 22, coil spring 36 can expand longitudinally, propelling needle holder assembly 32 rearwardly into needle retraction chamber 118. When body 22 is in the position shown in FIG. 16, any fluid present inside or rearwardly of annular fluid seal 34 is held there by frontal attachment 24. As shown in FIGS. 12-16, hub tube assembly 40 has been separated from hub guides 86, 88 of frontal attachment 64 and the portions of IV catheter introducer as shown can be disposed of in any manner that is approved as suitable for the disposal of such biologically contaminated products.

It will become apparent to those of ordinary skill in the art upon reading this specification in relation to the accompanying drawings that various other modifications and alterations can also be made to the embodiments disclosed here, and it is intended that the scope of the invention be limited only by the broadest interpretation of the appended claims to which the inventors are legally entitled.

We claim:

1. An intravenous catheter introducer for medical use comprising:
   a body;
   a frontal attachment disposed in transverse sliding engagement with a front part of the body;
   a hub tube assembly releasably supported by the frontal attachment, the hub tube assembly further comprising a hub, a cannula support and a flexible cannula tube projecting forwardly from the hub;
   a rearwardly biased needle holder assembly seated in the frontal attachment, the needle holder assembly comprising a base, a tubular needle holder projecting forwardly from the base along a first longitudinal axis coaxially aligned with an insertion needle projecting forwardly from the tubular needle holder through the hub tube assembly, and a spring support post projecting forwardly from the base along a second longitudinal axis passing through a compressed coil spring disposed around and slidably engaging the spring support post forwardly of the base but not surrounding the tubular needle holder with no part of the insertion needle projecting through any part of the compressed coiled spring; and
   wherein the body further comprises a needle retraction cavity that is offset laterally from the first longitudinal axis the insertion needle prior to needle retraction.

2. The intravenous catheter introducer of claim 1 wherein the insertion needle further comprises a proximal end disposed in fixed relation to the tubular needle holder.

3. The intravenous catheter introducer of claim 1 wherein the compressed coil spring abuts against the base around the spring support post to bias the needle holder assembly rearwardly against a forwardly facing surface of the body.

4. The intravenous catheter introducer of claim 1 wherein the body further comprises a fluid chamber that is coaxially aligned with the insertion needle prior to needle retraction.

5. The intravenous catheter introducer of claim 4 wherein an annular fluid seal is disposed between the needle holder assembly and the fluid chamber of the body to provide a fluid seal between the body and the frontal attachment.

6. The intravenous catheter introducer of claim 4 wherein a fluid sampling tool slidably engages a proximal end of the fluid chamber.

7. The intravenous catheter introducer of claim 6 wherein the fluid sampling tool further comprises a tool body, a forwardly projecting sampling tip, and a fluid sample reservoir disposed inside the tool body in fluid communication with the sampling tip and the fluid chamber.

8. The intravenous catheter introducer of claim 7 wherein the tool body further comprises a tubular filter housing disposed rearwardly of the fluid sample reservoir, the filter housing comprising a cylindrical bore and a filter seated in a proximal end of the cylindrical bore.

9. The intravenous catheter introducer of claim 1 further comprising a selectively removable needle cap that frictionally engages the frontal attachment.

10. The intravenous catheter introducer of claim 8 wherein the selectively removable needle cap further comprises a locking member configured to prevent lateral sliding movement between the body and the frontal attachment prior to vascular insertion of the insertion needle.

* * * * *